United States Patent [19]  [11] 4,150,044
Heinemann et al.  [45] Apr. 17, 1979

[54] PROCESS FOR THE MANUFACTURE OF 17α-HYDROXY-21-ACETOXY-PROGESTERONE

[75] Inventors: Henning Heinemann; Wolfgang Kreiser, both of Brunswick, Fed. Rep. of Germany

[73] Assignee: Hoechst Aktiengesellschaft, Frankfurt am Main, Fed. Rep. of Germany

[21] Appl. No.: 856,741

[22] Filed: Dec. 1, 1977

[30] Foreign Application Priority Data

Dec. 4, 1976 [DE] Fed. Rep. of Germany ....... 2655104

[51] Int. Cl.$^2$ ................................................ C07J 5/00
[52] U.S. Cl. ................................................ 260/397.47
[58] Field of Search ..................................... 260/397.47

[56] References Cited

PUBLICATIONS

Steroid Reactions by Djerassi et al. (1963) p. 586.

*Primary Examiner*—Elbert L. Roberts
*Attorney, Agent, or Firm*—Curtis, Morris & Safford

[57] ABSTRACT

The present invention relates to a process for the manufacture of 17α-hydroxy-21-acyloxy-progesterone, in particular of 17α-hydroxy-21-acetoxy-progesterone (Reichstein's substance S acetate) which is of great importance as a starting material for the manufacture of hydrocortisone.

2 Claims, No Drawings

PROCESS FOR THE MANUFACTURE OF 17α-HYDROXY-21-ACETOXY-PROGESTERONE

Several synthesis routes have already been described for building up the 17-hydroxyacetyl side-chain of steroids and especially of corticoids. However, all of these routes are characterized by a multiplicity of reaction stages.

As the importance of the total synthesis of steroids increases, the necessity for building up the 17-hydroxyacetyl side-chain in steroids from the corresponding 17-ketones becomes evident.

In particular, a process of this type is of interest for the manufacture of 17α-hydroxy-21-acetoxy-progesterone. This compound (Reichstein's substance S acetate) is of great importance as a starting material for the manufacture of Hydrocortisone.

The subject of the present invention is a process for the manufacture of 17α-hydroxy-21-acyloxy-progesterone (I)

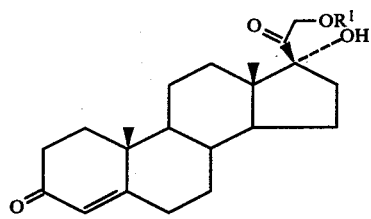

wherein $R^1$ represents the radical of an aliphatic carboxylic acid having 1-4 C atoms or the benzoyl radical, which is characterized in that (a) compound of the formula II

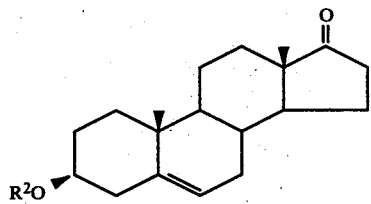

wherein $R^2$ denotes an easily detachable protective group, is reacted with a dialkoxyvinyl-lithium to give a compound of the formula III

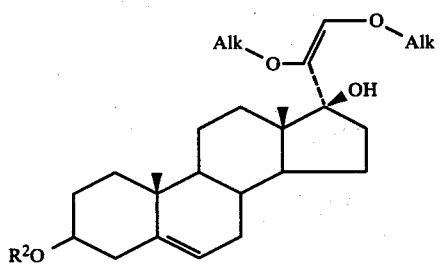

wherein $R^2$ denotes an easily detachable protective group and Alk denotes an alkyl group having 1-4 C atoms, (b) the resulting compound is converted, by treatment with a mineral acid in aqueous-alcoholic solution, to a compound of the formula IV

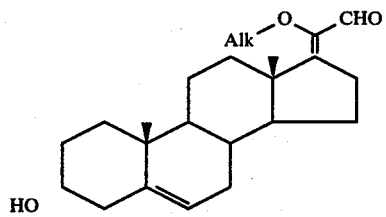

wherein Alk has the meaning indicated under the formula III, (c) the resulting compound is reduced to a compound of the formula V

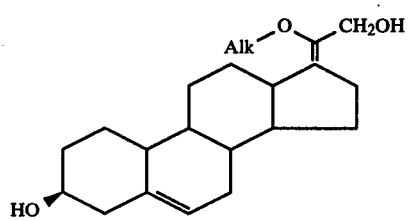

wherein Alk has the meaning indicated under formula III, (d) the resulting compound is converted into the monoacylate or diacylate of the formula VI

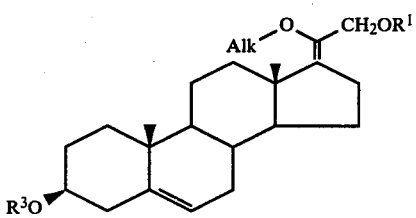

wherein Alk has the meaning indicated under formula III and $R^1$ has the meaning indicated under formula I and $R^3$ represents hydrogen or has the meaning of $R^1$, (e) the resulting compound is subjected to an Oppenauer oxidation to give a compound of the formula VII

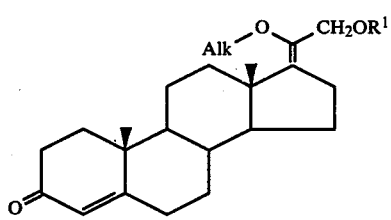

wherein Alk has the meaning indicated under formula III and $R^1$ has the meaning indicated under formula I, and (f) the resulting compound is oxidized with a percarboxylic acid to give a compound of the formula I.

The following substituents are preferred:

For $R^1$, the radical of a saturated, aliphatic carboxylic acid having 1-3 C atoms, especially the acetyl radical.

For $R^2$, a group of the formula —$CH_2$—O—R, wherein R represents an alkyl group having 1-4 C atoms, especially the group —$CH_2$—O—$CH_3$, and also the tetrahydropyranyl group and the 2,3-dihydropyranyl group.

For Alk, the methyl group.

The starting materials for the process according to the invention are known from the literature.

The first reaction stage is carried out by adding a solution of n-butyl-lithium in a saturated hydrocarbon, such as, for example, hexane, or an ether, dropwise to a dialkoxyethylene, preferably dimethoxyethylene, dissolved in an inert solvent, such as, for example, saturated hydrocarbons or tetrahydrofurane, in the presence of N,N,N',N'-tetramethylethylenediamine at temperatures between −40° C. and room temperature, preferably at 0° C., and under an inert gas and stirring the reaction mixture for ½ to 2 hours. A 17-keto-steroid of the formula II a or II b in an inert solvent, such as, for example, tetrahydrofurane, is then added and the resulting mixture is stirred for several hours. After acidifying with a mineral acid, the reaction mixture is taken up in ethyl acetate and worked up in the customary manner.

In the subsequent reaction stage the resulting enol-ether is split by heating with 1-10% strength mineral acid in an alcoholic medium. Preferably, the reaction is carried out by boiling the enol-ether with a 1% strength aqueous-ethanolic solution of hydrochloric acid for 30 minutes under gentle reflux. After the solvent has been largely distilled off under reduced pressure, the residue is taken up in ethyl acetate, neutralized and worked up in the customary manner. The reaction product is purified, for example, by preparative thin layer chromatography.

The reduction of the formyl group in the compound of the formula IV is effected in a conventional manner with a complex metal hydride, such as, for example, lithium aluminum hydride, lithium borohydride, sodium borohydride or lithium tri-tert.-butoxy-aluminum hydride.

The acylation of the compounds of the formula V is also effected by customary methods.

The Oppenauer oxidation according to process step e) is carried out, for example, in accordance with the instructions in "Organikum" ("Organic Chemistry"), VEB Deutscher Verlag der Wissenschaften, 10th edition 1972, page 541. Preferably, the 21-monoacylate is reacted.

In order to introduce the 17-OH group, the resulting compound of the formula VII is reacted with a percarboxylic acid, such as performic acid, peracetic acid or perbenzoic acid and preferably with m-chloroperbenzoic acid, at temperatures of −20° to +20° C., preferably at 0° C., in an inert solvent, for example a chlorinated aliphatic hydrocarbon, such as carbon tetrachloride or chloroform, whilst stirring. After neutralizing with an aqueous solution of an alkali metal carbonate or alkali metal bicarbonate, the reaction mixture is taken up in ethyl acetate and worked up in the customary manner.

It was not foreseeable that the splitting of the enol-ether (stage b) would proceed under the conditions according to the invention, since it had to be assumed that only mild hydrolysis processes, such as reaction with oxalic acid in methanol/water (R. Stevenson and L. F. Fieser, J. Am. Chem. Soc. 78, 1409 (1956)), with p-toluenesulfonic acid in dioxane (J. H. Fried, A. N. Nutile and G. E. Arth, J. Am. Chem. Soc. 82 5704 (1960)) or with methanolic aqueous acetic acid (J. E. Baldwin, G. A. Hofle and O. W. Lever Jr., J. Am. Chem. Soc. 96, 7125(1974)) could lead to a successful result. However, when these reactions were carried out either no reaction took place or oily reaction products formed which could not be separated. It is also surprising that the splitting of the enol-ether proceeds selectively.

The resulting compound of the formula I can be hydrolyzed by conventional methods to 17α,21-dihydroxy-progesterone (Reichstein's substance S), which can be converted, for example microbiologically according to the method of D. R. Colingsworth et al (J. Am. Chem. Soc. 74, 2381 (1952)) or F. R. Hanson et al (J. Am. Chem. Soc. 75, 5369 (1953)), into hydrocortisone, which has a powerful antiphlogistic action:

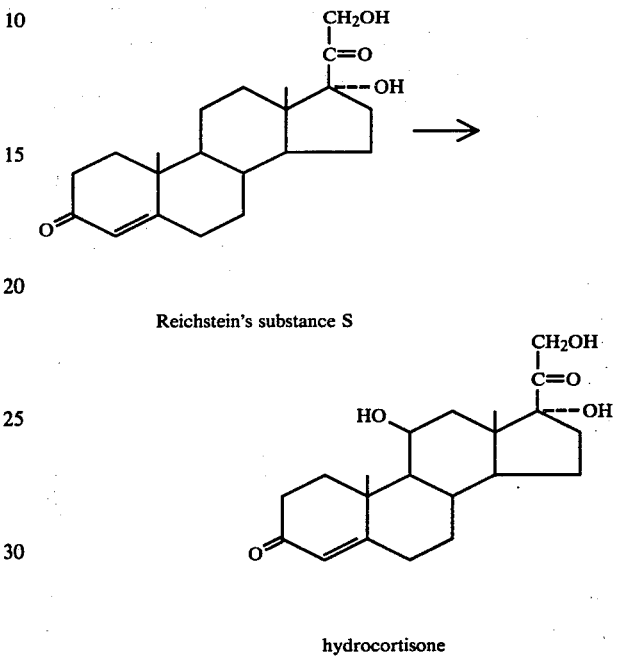

Reichstein's substance S hydrocortisone

EXAMPLE

Preparation of the starting compound:

3-methoxymethyl-dihydro-epi-androsterone (II)

5 g of dehydro-epi-androsterone are dissolved in 10 ml of absolute tetrahydrofurane. 25 ml of methylal are added to this solution and, after cooling to 0° C., 0.5 ml of freshly distilled POCl$_3$ is added, while stirring. The reaction solution is allowed to warm to room temperature and after 48 hours is worked up in the conventional manner with ethyl acetate/sodium bicarbonate solution.

Yield: 5.75 g of colorless crystals (quantitative).

Melting point: 27–128°

| NMR spectrum: | | | | |
|---|---|---|---|---|
| 0.90 ppm | Sg | 3 H | 18-CH$_3$ | |
| 1.06 ppm | Sg | 3 H | 19-CH$_3$ | |
| 3.38 ppm | Sg | 3 H+) | methyl group | } of the methoxy-methyl ether |
| 4.70 ppm | Sg | 2 H | methylene group | |
| 5.40 ppm | Mu | 1 H | 6-H | |

+)The integration shows 4 protons because the broad multiplet of the 3α-H is additionally under the singlet.

$C_{21}H_{32}O_3$ (molecular weight 332.4).

(a)

3β-methoxymethyl-17β-hydroxy-17α-trans-1,2-dimethoxyvinyl-Δ$^5$-androstene (III)

60 ml of n-butyl-lithium (20% strength in hexane) are added dropwise at 0°, under a nitrogen atmosphere, to 35 ml of dimethoxyethylene and 30 ml of tetramethylethylenediamine. The ice-cooling is removed and the mixture is then stirred for a further one hour at room temperature. 5.5 g of II, dissolved in 60 ml of absolute tetrahydrofurane, are then added dropwise in the course of 20 minutes and the resulting mixture is stirred for a further 5 hours at room temperature. For working up, the reaction mixture is weakly acidified with 10% strength sulfuric acid, while cooling with ice, and the customary procedure is then followed. Purification is effected by preparative layer chromatography (cyclohexane/ethyl acetate=5:1, developed 3 times) and subsequent crystallization from methylene chloride/ether (colorless crystals).

Yield: 5.8 g (83.7% of theory).
Melting point: 156–157°.

| NMR spectrum: | | | |
| --- | --- | --- | --- |
| 0.88 ppm | Sg | 3H | 18-$CH_3$ |
| 1.02 ppm | Sg | 3H | 19-$CH_3$ |
| 3.34 ppm | Sg | 3H | 3-$OCH_2$—$OCH_3$ |
| 3.46 ppm | Sg | 3H ⎫ | |
| | | | 20-$OCH_3$, 21-$OCH_3$ |
| 3.51 ppm | Sg | 3H ⎭ | |
| 3.97 ppm | Sg | 1H | 17β-OH |
| 4.67 ppm | Sg | 2H | 3-$OCH_2O$— |
| 5.40 ppm | Mu | 1H | 6-H |
| 5.71 ppm | Sg | 1H | 21-H |

IR spectrum (KBr): 3350 $cm^{-1}$ OH

| Optical rotation ( = 0.77 g/100 ml of $CHCl_3$): | |
| --- | --- |
| at 578 nm [α] | = − 52.60° |
| 546 nm | = − 61.04° |
| 436 nm | = −103.90° |
| 405 nm | = −122.73° |
| 364 nm | = −154.55° |

| Mass spectrum: | | |
| --- | --- | --- |
| $M^+$ | (mole mass) | 420 |
| m/e | ($M^+$−$H_2O$) | 402 |
| m/e | ($M^+$−$H_3CO$ · ) | 389 |

| Elementary analysis: $C_{25}H_{40}O_5$ (molecular weight = 420.6) | |
| --- | --- |
| calculated C: 71.39% | found C: 71.34% |
| H: 9.59% | H: 9.52% |

(b)
Z-3β-hydroxy-17-(methoxy-formyl-methylidene)-Δ⁵-androstene (IV)

5.5 g of III are dissolved in 180 ml of ethanol. 18 ml of water and 2 ml of concentrated hydrochloric acid are added to this solution at room temperature, while stirring. This solution is heated under gentle reflux for 30 minutes. The solvent is then largely stripped off and the residue which remains is worked up in the customary manner.

The product mixture is separated via a dry column (size 30 mm, packing: 200 g of silica gel for dry column chromatography, eluent: cyclohexane/ethyl acetate =3:1).

Two colorless products can be isolated and of these the less polar compound is IV.

Yield: 2.04 g (45.3% of theory); melting point 185–6° C.

| NMR spectrum: | | | |
| --- | --- | --- | --- |
| 0.98 ppm | Sg | 3H | 18-$CH_3$ |
| 1.04 ppm | Sg | 3H | 19-$CH_3$ |
| 3.54 ppm | Mu | 1H | 3α-H |
| 3.64 ppm | Sg | 3H | 20-$OCH_3$ |
| 5.36 ppm | Mu | 1H | 6-H |
| 9.69 ppm | Sg | 1H | aldehyde-H |

| IR spectrum (KBr): | |
| --- | --- |
| 3,380 $cm^{-1}$ | OH |
| 1,673 $cm^{-1}$ | carbonyl (unsaturated aldehyde) |

UV spectrum ($CH_2Cl_2$): $\lambda_{max}$ = 265 nm; $\epsilon$ = 11,500.

| Optical rotation (c = 0.72 g/100 ml of $CHCl_3$): | |
| --- | --- |
| at 578 nm [α] | = − 70.14° |
| 546 nm | = − 42.36° |
| 436 nm | = + 95.83° |
| 405 nm | = + 269.44° |

| Mass spectrum: | | |
| --- | --- | --- |
| $M^+$ | (mole mass) | 344 |
| m/e | ($M^+$−$CH_3$ · ) | 329 |
| m/e | ($M^+$−$OCH_3$) | 313 |
| m/e | ($M^+$−$OCH_3$ · −$H_2O$) | 295 |

| Elementary analysis: $C_{22}H_{32}O_3$ (molecular weight = 344.5) | |
| --- | --- |
| calculated C: 76.70% | found C: 76.66% |
| H: 9.36% | H: 9.40% |

The by-product is 3β,17β-dihydroxy-17α-methoxyacetyl-Δ⁵-androstene with a melting point of 134–5° C.

(c)
Z-3β-hydroxy-17-(1-methoxy-2-hydroxy-ethylidene)-Δ⁵-androstene (V)

A solution of 1.9 g of IV in 30 ml of absolute tetrahydrofurane is added dropwise in the course of 10 minutes, at −25°, while stirring, to a suspension of 190 mg of lithium aluminum hydride in 25 ml of absolute ether. The mixture is stirred for a further 50 minutes at this temperature and excess lithium aluminum hydride is then carefully decomposed with water. Working up is carried out with ethyl acetate and saturated ammonium chloride solution is used for washing. The product is obtained as a colorless powder.

Yield: 1.9 g $C_{22}H_{34}O_3$ (molecular weight =346.5).
The product is identified in the form of the diacetate.

(d₁)
Z-3β-acetoxy-17-(1-methoxy-2-acetoxyethylidene)-Δ⁵-androstene (VI)

150 mg of V are dissolved in 5 ml of pyridine and 2 ml of acetic anhydride are added. This solution is heated for 30 minutes on a boiling water bath. The solvent is then largely stripped off under reduced pressure and the residue is worked up in the customary manner. The product is crystallized from ether/cyclohexane.

Yield: 1.69 g (91.2% relative to aldehyde IV).
Melting point: 142–143°.

| NMR spectrum: | | | |
|---|---|---|---|
| 0.90 ppm | Sg | 3H | 18-CH$_3$ |
| 1.04 ppm | Sg | 3H | 19-CH$_3$ |
| 2.01 ppm | Sg | 3H | 3-acetate |
| 2.07 ppm | Sg | 3H | 21-acetate |
| 3.50 ppm | Sg | 3H | 20-OCH$_3$ |
| 4.64 ppm | Mu | 3H | 21-CH$_2$; 3α-H |
| 5.40 ppm | Mu | 1H | 6-H |

| IR spectrum (KBr): | |
|---|---|
| 1,731 cm$^{-1}$ | acetate (3; 21) |
| 1,250 cm$^{-1}$ | |

| Optical rotation (c = 1.906 g/100 ml of CHCl$_3$) | |
|---|---|
| at 578 nm [α] | = − 67.16° |
| 546 nm | = − 77.65° |
| 436 nm | = − 136.94° |
| 405 nm | = − 167.37° |
| 364 nm | = − 226.13° |

| Mass spectrum: | | |
|---|---|---|
| M$^+$ | (mole mass) | 430 |
| m/e | (M$^+$ − CH$_3$) | 415 |
| m/e | (M$^+$ − AcOH) | 370 |
| m/e | (M$^+$ M CH$_3$ − AcOH) | 355 |
| m/e | (M$^+$ − 2 AcOH) | 310 |
| m/e | (M$^+$ − CH$_3$ − 2 AcOH) | 295 |

| Elementary analysis: C$_{26}$H$_{38}$O$_5$ (molecular weight = 430.6) | |
|---|---|
| calculated C: 72.52% | found C: 72.46% |
| H: 8.90% | H: 8.83% |

(d$_2$)
Z-3β-hydroxy-17-(1-methoxy-2-acetoxyethylidene)-6 6$^5$-androstene (VI)

1.65 g of V are dissolved in 15 ml of pyridine and the solution is cooled to 0°. 0.5 ml of acetic anhydride are added to this solution, while stirring. The solution is left to stand at 5° for 12 hours, excess saturated sodium bicarbonate solution is then added and the mixture is worked up in the customary manner.

Yield: 1.69 g (91.2%, relative to aldehyde IV).
Melting point: 142–143°.

| NMR spectrum: | | | |
|---|---|---|---|
| 0.90 ppm | Sg | 3H | 18-CH$_3$ |
| 1.02 ppm | Sg | 3H | 19-CH$_3$ |
| 2.07 ppm | Sg | 3H | 21-acetate |
| 3.18 ppm | Mu | 1H | 3β-OH |
| 3.49 ppm | Sg | 3H$^+$) | 20-OCH$_3$ |
| 4.62 ppm | Mu | 2H | 21-CH$_2$ |
| 5.35 ppm | Mu | 1H | 6-H |

| IR spectrum (KBr): | |
|---|---|
| 3,325 cm$^{-1}$ | OH |
| 1,728 cm$^{-1}$ | acetate |
| 1,250 cm$^{-1}$ | |

| Optical rotation (c = 2.026 g/100 ml of CHCl$_3$): | |
|---|---|
| at 578 nm [α] | = − 75.52° |
| 546 nm | = − 87.36° |
| 436 nm | = − 154.00° |
| 405 nm | = − 187.07° |
| 364 nm | = − 249.75° |

| Mass spectrum: | | |
|---|---|---|
| M$^+$ | (mole mass) | 388 |
| m/e | (M$^+$ − CH$_3$.) | 373 |
| m/e | (M$^+$ − AcOH) | 328 |
| m/e | (M$^+$ − AcOH − CH$_3$.) | 313 |

| Elementary analysis: C$_{24}$H$_{36}$O$_4$ (molecular weight = 388.5) | |
|---|---|
| calculated C: 74.19% | found C: 74.22% |
| H: 9.34% | H: 9.39% |

(e)
Z-17-(1-methoxy-2-acetoxyethylidene)-Δ$^4$-androsten-3-one (VII)

1.5 g of VI are dissolved in 90 ml of absolute benzene and 30 ml of absolute acetone and after adding 1.8 g of aluminum tertiary butylate the mixture is boiled under reflux for 10 hours. It is then slightly acidified with dilute sulfuric acid and worked up in the customary manner.

The crude product is separated by preparative layer chromatography (cyclohexane/ethyl acetate = 3:1, developed twice).

Yield: 1.17 g (78.1% of theory).
Melting point: 135–136°.

| NMR spectrum: | | | |
|---|---|---|---|
| 0.93 ppm | Sg | 3H | 18-CH$_3$ |
| 1.22 ppm | Sg | 3H | 19-CH$_3$ |
| 2.07 ppm | Sg | 3H | 21-acetate |
| 3.51 ppm | Sg | 3H | 20-OCH$_3$ |
| 4.63 ppm | Mu | 2H | 21-CH$_3$ |
| 5.77 ppm | "Sg" | 1H | 4-H |

| IR spectrum (KBr): | |
|---|---|
| 1,732 cm$^{-1}$ | acetate |
| 1,668 cm$^{-1}$ | unsaturated ketone |
| 1,618 cm$^{-1}$ | = C-H |
| 1,235 cm$^{-1}$ | acetate |

UV spectrum (CH$_2$Cl$_2$): λ$_{max}$ = 240 nm; ε = 18,200.

| Optical rotation (c = (0.713 g/100 ml of CHCl$_3$): | |
|---|---|
| at 578 nm [α] | = 128.12° |
| 546 nm | = 142.18° |
| 436 nm | = 218.13° |
| 405 nm | = 243.75° |
| 364 nm | = 288.17° |

| Mass spectrum: | | |
|---|---|---|
| M$^+$ | (mole mass) | 386 |
| m/e | (M$^+$ − CH$_3$.) | 371 |
| m/e | (M$^+$ − AcOH) | 326 |

-continued

| Mass spectrum: | | |
|---|---|---|
| m/e | (M⁺ — AcOH — CH₃.) | 311 |

| Elementary analysis: $C_{24}H_{34}O_4$ (molecular weight = 386.5) | |
|---|---|
| calculated C: 74.57% | found C: 74.52% |
| H: 8.87% | H: 8.82% |

(f) 17α-hydroxy-21-acetoxy-progesterone, Reichstein's substance S acetate (I)

1.05 g of VII are dissolved in 50 ml of chloroform and the solution is cooled to 0°. A solution, which has previously been brought to 0°, of 1 g m-chloro-perbenzoic acid in 40 ml of chloroform is then added dropwise very rapidly and the mixture is stirred for a further 30 seconds and neutralized with a saturated solution of sodium bicarbonate. It is then worked up with ethyl acetate in the customary manner and the resultant viscous yellow oil is separated by means of preparative layer chromatography (cyclohexane/ethyl acetate = 3:1, developed 3 times) and the product is left to crystallize from ether.

Yield: 550 mg (52.7% of theory).

Melting point: 234–237°(*).

(*) literature: melting point: 236–238° (K. Miescher and J. Schmidlin, Helv. Chim. Acta. 33, 1840 (1950)).

In respect of all of its physical and spectroscopic data, the resulting product is identical to an original sample; a mixed melting point shows no depression.

What is claimed is:

1. A process for making a 17α-hydroxy-21-acyloxy progesterone of the formula

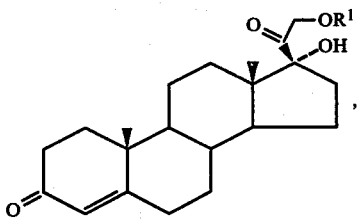

wherein R¹ is benzoyl or aliphatic acyl having 1 to 4 carbon atoms, which comprises reacting a dialkoxyvinyl-lithium having 1 to 4 carbon atoms in each alkoxy group thereof with a compound of the formula

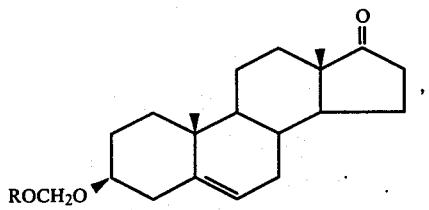

wherein R is alkyl having 1 to 4 carbon atoms, to give a compound of the formula

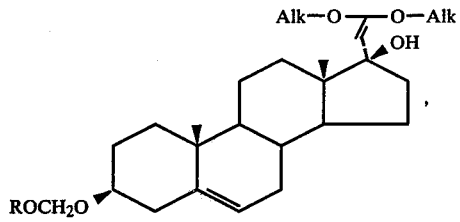

wherein Alk is alkyl having 1 to 4 carbon atoms, treating this last-mentioned compound with a mineral acid in aqueous-alcoholic solution to give a compound of the formula

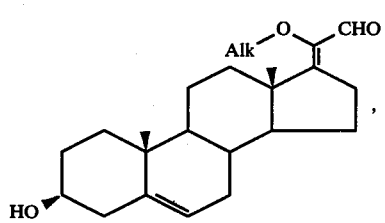

reducing this last-mentioned compound with a complex metal hydride to give a compound of the formula

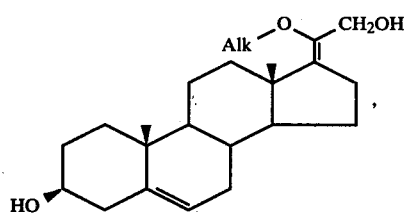

reacting the last-mentioned compound with an acylating agent containing the R¹ group to give a compound of the formula

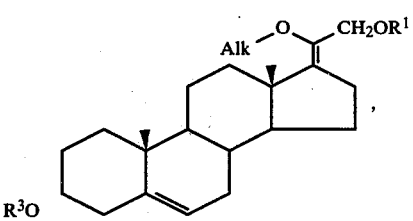

wherein R³ is hydrogen or R¹, subjecting the last-mentioned compound to an Oppenauer oxidation to give a compound of the formula

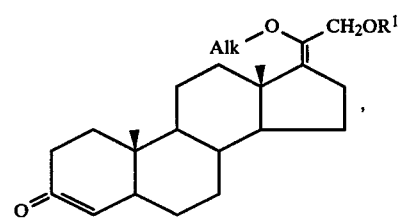

and then oxidizing the last-mentioned compound with a percarboxylic acid to give the desired 17α-hydroxy-21-acyloxy progesterone.

2. A process as in claim 1 wherein R¹ is acetyl.

* * * * *